United States Patent
Lastella et al.

(10) Patent No.: US 9,636,088 B2
(45) Date of Patent: May 2, 2017

(54) FECAL SAMPLING DEVICE

(71) Applicant: IMMUNOSTICS, INC., Ocean, NJ (US)

(72) Inventors: Vincent P. Lastella, Clark, NJ (US); Kenneth Kupits, Lanoka Harbor, NJ (US)

(73) Assignee: IMMUNOSTICS, INC., Ocean, NJ (US)

( * ) Notice: Subject to any disclaimer, the term of this patent is extended or adjusted under 35 U.S.C. 154(b) by 0 days.

(21) Appl. No.: 14/573,131

(22) Filed: Dec. 17, 2014

(65) Prior Publication Data

US 2016/0174947 A1    Jun. 23, 2016

(51) Int. Cl.
*A61B 10/00* (2006.01)
*B01L 3/00* (2006.01)
*G01N 33/50* (2006.01)
*G01N 33/52* (2006.01)
*G01N 35/00* (2006.01)

(52) U.S. Cl.
CPC ........ *A61B 10/0038* (2013.01); *B01L 3/5055* (2013.01); *B01L 2200/025* (2013.01); *B01L 2300/069* (2013.01); *B01L 2300/0809* (2013.01); *B01L 2300/0887* (2013.01); *B01L 2300/126* (2013.01); *G01N 33/50* (2013.01); *G01N 33/525* (2013.01); *G01N 35/00029* (2013.01); *Y10S 435/97* (2013.01)

(58) Field of Classification Search
CPC ............ G01N 33/525; G01N 35/00029; Y10S 435/97
USPC ...... 436/518, 66, 64; 435/970; 422/421, 551
See application file for complete search history.

(56) References Cited

U.S. PATENT DOCUMENTS

| | | | |
|---|---|---|---|
| 3,965,888 A * | 6/1976 | Bender | ........................ 600/572 |
| 4,055,394 A * | 10/1977 | Friedman | ......... G01N 33/54386 422/401 |
| 4,559,949 A * | 12/1985 | Levine | ................. G01N 33/521 422/409 |
| 7,427,505 B2 | 9/2008 | LaStella | |
| D596,753 S | 7/2009 | LaStella | |
| D598,121 S | 8/2009 | LaStella | |
| 8,304,596 B2 | 11/2012 | LaStella | |
| 8,679,420 B2 | 3/2014 | LaStella et al. | |
| 8,679,848 B2 | 3/2014 | LaStella | |
| 2006/0018794 A1* | 1/2006 | LaStella | ......................... 422/99 |
| 2008/0241940 A1 | 10/2008 | LaStella | |
| 2009/0238720 A1* | 9/2009 | Kikta | ............................. 422/58 |

(Continued)

*Primary Examiner* — Dennis M White
*Assistant Examiner* — Bryan Kilpatrick
(74) *Attorney, Agent, or Firm* — Stroock & Stroock & Lavan LLP

(57) ABSTRACT

A specimen collection or a specimen collection and testing device having an embossed or raised section. In one embodiment the device includes a first panel with one or more apertures for receiving specimen and a second panel having a removable tab, the removable tab aligned with the one or more apertures when the device is assembled such that depositing specimen through the one or more apertures deposits the specimen on the removable tab. A cover has one or more embossed (or raised) sections that align with the one or more apertures when the cover overlays the first panel, thus helping to prevent adherence of the specimen to the inner surface of the cover.

6 Claims, 6 Drawing Sheets

(56) References Cited

U.S. PATENT DOCUMENTS

2011/0027903 A1    2/2011   LaStella
2015/0056637 A1    2/2015   Lastella

* cited by examiner

FECAL SAMPLING DEVICE

BACKGROUND OF THE INVENTION

1. Field of the Invention

The present invention relates, generally, to specimen collection and more particularly, to devices for collecting and/or determining the presence of occult blood in fecal matter.

2. Description of Related Art

Over 100,000 persons per year in the United States are afflicted with cancer of the colon and rectum. When the number of colon/rectal cancers occurring each year is combined with the number of cancers occurring in other digestive organs, including the esophagus and stomach, such cancers of the digestive system account for more occurrences of cancer than any other single form of the disease. Contrary to many other forms of cancer, early diagnosis and treatment of digestive tract cancer does result in a cure rate of 80% to 90%. If, however, the disease is not detected until the later stages, the cure rate drops significantly. Thus, early detection of the disease is important to successful treatment of digestive tract cancer.

Most, but not all, cancers of the digestive tract bleed to a certain extent. This blood is deposited on and in fecal matter excreted from the digestive system. The presence of blood in fecal matter is not normally detected, however, until gross bleeding, that is, blood visible to the naked eye, occurs. Gross bleeding, however, is symptomatic of advanced cancers.

Digestive tract cancers in the early stages, including pre-cancerous polyps, also tend to bleed, giving rise to occult (hidden) blood in the fecal matter. Other pathological conditions, such as Crohn's disease and diverticulitis, can also give rise to the presence of occult blood in the fecal matter.

It is known that because of the relatively high fat content of fecal matter, blood, when present, is not distributed uniformly throughout it. For this reason, obtaining multiple specimens from different areas of each bowel movement is desirable; but even a single positive test from any part of the feces should be considered a positive result.

Accordingly, test equipment and test procedures have been developed for use by physicians in testing for the presence of occult blood in fecal matter. One such test is disclosed in Pagano U.S. Pat. No. 3,996,006. In general, the Pagano test employs an absorbent paper or sheet impregnated with a guaiac reagent and encased in a special test slide having openable flaps on both sides of the test slide. To use the Pagano test slide, a specimen of fecal matter is smeared onto the guaiac impregnated paper by opening the panel or cover on one side (front) of the test slide and applying the specimen through apertures or "wells." Thereafter, the cover is closed. The panel on the opposite side (rear) of the test slide is then opened and a nonaqueous developing solution is applied to the guaiac impregnated paper. If occult blood is present in the fecal matter smeared on the opposite side of the paper, the guaiac reaction will dye the paper blue, providing a positive indication of the presence of blood in the fecal matter.

A specific test for human hemoglobin (often referred to as an immunological or immunochemical test) has also been devised. This test theoretically registers only human hemoglobin and not animal blood from meat or other agents, and therefore, theoretically does not require the patient to be on a special diet. While the hemoglobin test has the advantage over guaiac tests of registering only human hemoglobin, the hemoglobin test is expensive for a screening test and requires specially trained individuals to perform and read the test. Such hemoglobin tests may also be administered using a slide-type devices. For example, devices may be used to collect a specimen on a removable tab, which may be removed, carrying with it the specimen for off-device testing using a hemoglobin test.

Certain potential disadvantages of the existing devices have been observed. For example, although appropriate materials are used in constructing the device, the cardboard and paper materials typically used in the construction of test devices is subject to deterioration when placed in contact with the moisture-containing specimens. Consequently, there exists a need for improved testing devices.

SUMMARY

According to an embodiment of the present invention, a novel device having an embossed or raised section is disclosed for specimen collection or specimen collection and testing. The device preferably includes a first panel with one or more apertures for receiving specimen and a second panel having a removable tab, the removable tab aligned with the one or more apertures when the device is assembled such that depositing specimen through the one or more apertures deposits the specimen on the removable tab. The device further includes a cover having one or more embossed (or raised) sections that align with the one or more apertures when the cover overlays the first panel, thus helping to prevent adherence of the specimen to the inner surface of the cover.

BRIEF DESCRIPTION OF THE DRAWINGS

The invention will now be described with reference to the accompanying drawings, in which.

DETAILED DESCRIPTION OF EMBODIMENTS

Various embodiments of the invention, including the devices of FIGS. 1-3 intended only for collecting specimens for off-device testing (i.e., no on-device testing by depositing developing solution on the device), as well as the devices of FIGS. 4-6 intended for both on-device and off-device testing, will now be described. In general, the illustrative devices include specimen collection apertures (or wells) for receiving specimen on a removable tab. The device cover includes one or more embossed (or raised) areas aligned with the apertures, which provide a space for the specimen, such that when the specimen is collected and the cover is closed, the specimen is less likely to adhere to the cover.

Figure 1:
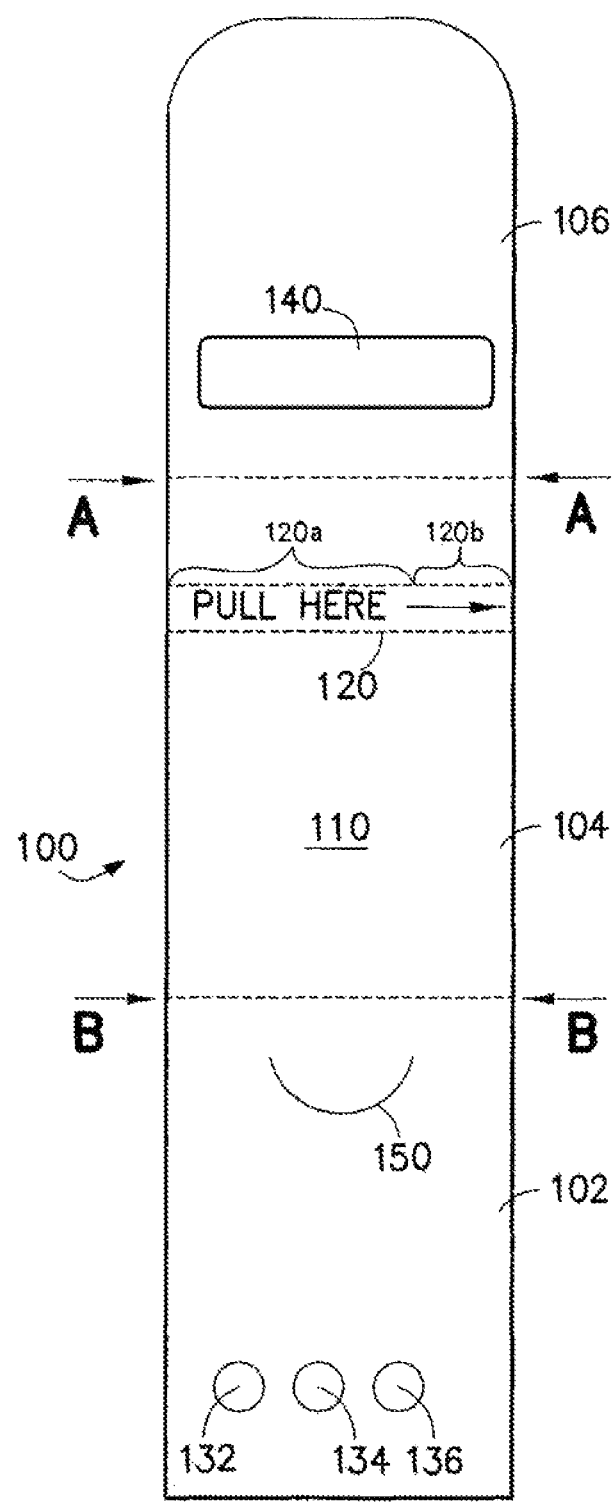
FIG. 1 is a front plan view of a device according to one embodiment of the invention showing the cover containing an embossed section.

Turning now to FIG. 1, device 100 is shown an unassembled state. When assembled, first panel 102 is folded along line B on top of second panel 104, and cover 106 is folded along line A, to cover first panel 102. The device 100 includes a test area 110, a first panel 102, a second panel 104 and a cover 106. The device 100 is assembled as noted above without a sheet between the first panel 102 and second panel 104. However, a sheet may be used, for example, to meter the amount of specimen collected. The first panel 102 includes multiple apertures, 132, 134, 136, which are aligned off center within test area 110. In alternate embodiments one or some other number of apertures are included. The second panel 104 includes removable tab 120, which has a first portion 120a and a second portion 120b.

The panels 102, 104 and cover 106 are preferably provided with a layer of non-stick material, typically a wax layer although other materials may be used. Despite the inclusion of a non-stick material, it has been discovered that the covers may stick to the specimens, which may lead to either an amount of a specimen being left on the inside surface of a cover when the corresponding tab is removed, or the removal of a piece of the inner surface of the cover when a corresponding tab is removed.

To help prevent or minimize the extent of the foregoing, cover 106 includes section 140, which is raised with respect to the inner surface of the cover 106 (for example, created by embossing the cover or removing a portion of the cover's thickness from the inner surface) (referred to herein as embossed section). Embossed section 140 is positioned such that when the cover 106 is closed, the embossed section 140 aligns with the group of apertures 132, 134, 136, thereby providing additional space for collected specimens. In alternate embodiments, rather than a single embossed area corresponding to the group of apertures 132, 134, 136, a separate embossed area is provided corresponding to each aperture (for example, as shown in FIGS. 4-6). Preferably the embossed section 140 is created by embossing the section of the cover that aligns with the aperture(s) by about 1/64 of an inch. It should be understood that embossments having a depth greater than 1/64 inch may be used, depending on the tear strength of the particular material used for the panel.

Figure 2:
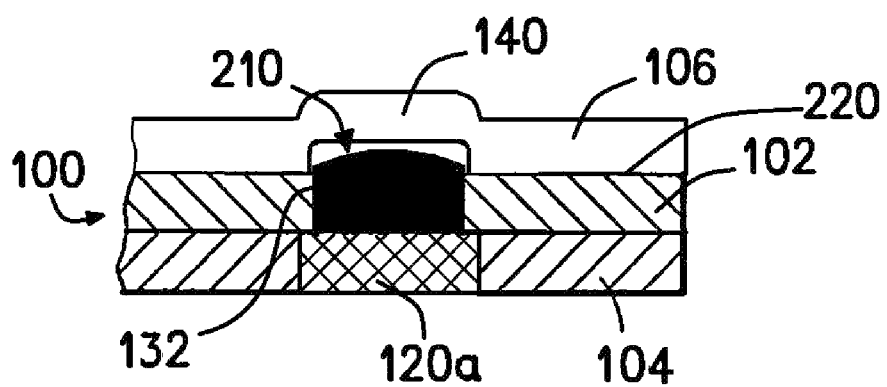
FIG. 2 is a cross-sectional view of the embodiment of the present invention illustrated in FIG. 1 after obtaining a specimen and being assembled.

The structure and effect of embossed section 140 is further shown in FIG. 2, which is a cross section taken through a representative one of the apertures (e.g., 132) of device 100 after the device 100 has been assembled and used to obtain a specimen 210. The specimen 210 has been applied to the device, through the aperture, and rests on the first portion 120a of the removable tab 120. As noted, the device 100 is generally constructed such that the second portion 120b of the tab 120 is not aligned with the apertures and can be used to remove the tab 120 as a specimen-free grasping area, without contaminating the specimen 210. The cover 106 has been folded onto the first panel 102 to close the device 100. Cover 106 includes an embossed section 140 that serves to provide a relatively larger area between the tab 120 and the interior surface of the cover 106 for housing the specimen 210. In other words the embossed section 140 (as with the other embodiments described herein) provides a space that is aligned with the aperture and is above the plane of the top surface 220 of the first panel 102. The increased volume created by the embossed section 140 helps to prevent material of the inner surface of the cover 106 from adhering to the specimen 210 and thus preventing specimen from being left behind on the inner surface of the cover 106, when the tab 120 is removed to test the specimen 210.

Turning back to FIG. 1, to assemble, first panel 102 is folded along line B such that panel 102 is in contact with panel 104. Cover 106 is similarly folded along line A, on to panel 102 and secured in arcuate slit 150. When assembled, the apertures 132, 134, 136, are aligned with removable tab 120 and the embossed section 140 of the cover 106 is aligned with the apertures 132, 134, 136. More specifically, the off-center configuration of the apertures 132, 134, 136, cause them to be aligned only with the first portion 120a of the removable tab 120, and not aligned with the second portion 120b. As a result, specimens applied to any of the apertures 132, 134, 136, only come into contact with the first portion 120a of tab 120 and do not come into contact with the second portion 120b of tab 120. This allows the second portion 120b of the tab 120 to be used as a specimen-free grasping area, to remove the tab 120 from the device 100 without contaminating the specimen. Since specimens collected with the device 100 are not intended to be tested until removed, the device 100 is preferably reagent free.

Although the apertures 132, 134, 136 are illustrated as round, alternate embodiments have other shapes and sizes. Also, although the embodiment is shown with three apertures, one or some other number of apertures may be used.

In other alternate embodiments based on that of FIGS. 1 and 2, a sheet (or other filtering or metering material) may be placed between the first and second panel to meter the amount of specimen removed with the tab.

According to an additional embodiment, the testing device may be provided individually or may be packaged in kit form. For example, kits might be prepared comprising numerous testing devices, reagents required to perform the primary analysis for such devices, such as the developing solution used in the guaiac test, sample tubes in which to place the tabs and perforated zones from the sheet and materials for a secondary test, such as, but not limited to, a specific immunochemical test, such as an ELISA, Lateral Flow Device, or any testing procedure used for human blood.

The test tubes may be pre-filled with the test reagents or they may be provided separately. To reduce costs, the kit may contain fewer immunochemical test reagents than primary test reagents given the use of the immunochemical test in a confirmatory role.

Figure 3:
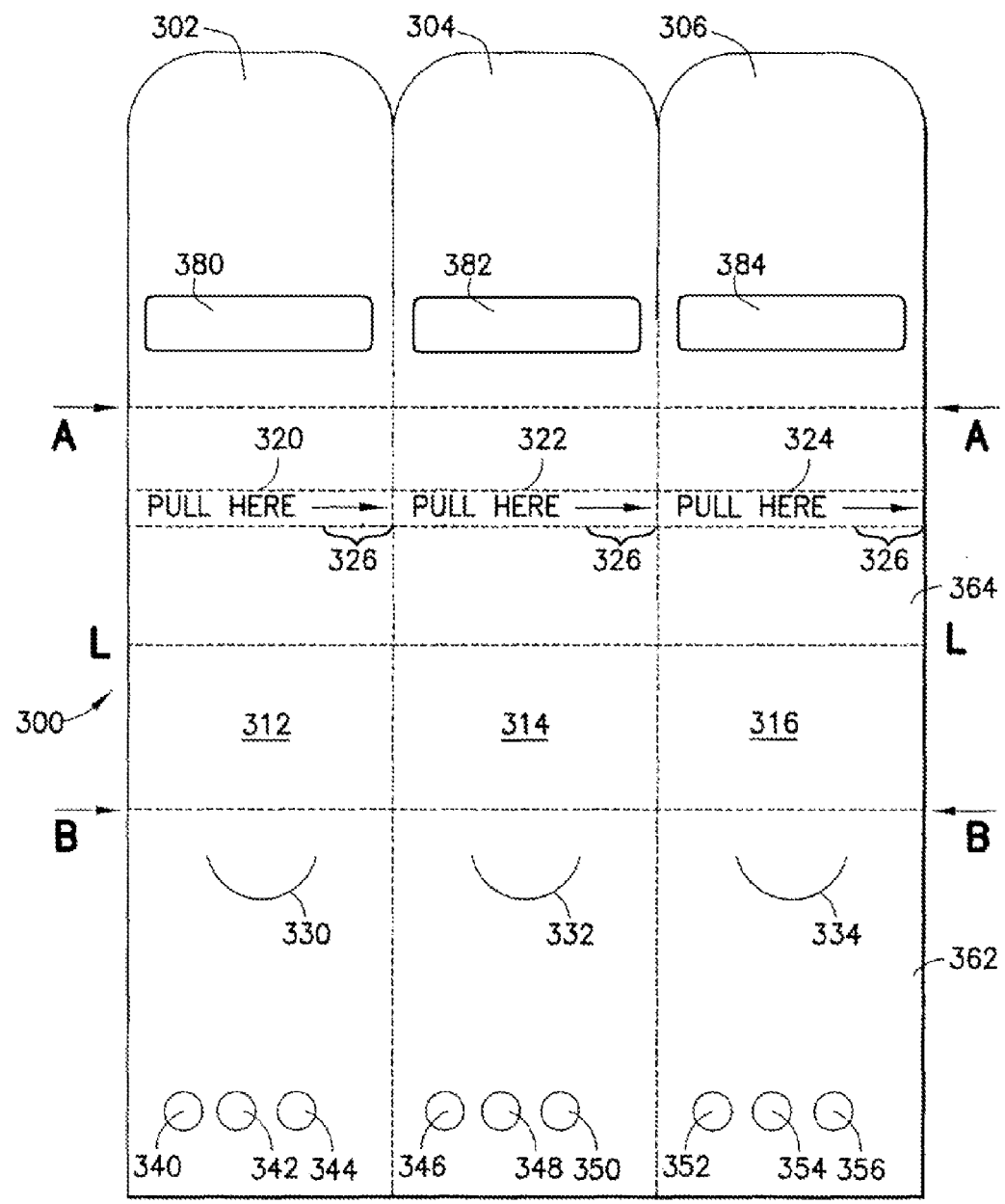
FIG. 3 is a front plan view of a sampling device in an un-assembled state according to an alternate embodiment of the invention.

Furthermore, although the device 100 as shown has a single specimen collection area, multiple collection areas may be formed together as shown in FIG. 3. As shown therein device 300 generally includes three test areas 312, 314, 316 and is formed of a first panel 362 and a second panel 364. Panels 362, 364 and covers 302, 304, 306 can be formed of a single sheet of paper, cardboard or other suitable material, in which the apertures, slits, tabs and perforations are die-cut. The device 300 is assembled by folding the sheet along line A-A and line B-B, thereby overlaying panel 362 on to panel 364 and the covers 302, 304, 306 on to first panel 362. The assembly is held together with a suitable glue or adhesive. It should be understood that panels 362 and 364 may be constructed separately and then assembled (e.g., glued along a portion of the edges) to form the device (as is also the case with the other embodiments described herein).

Each test area 312, 314, 316 is configured to receive specimens through three apertures, which can be situated transversely, or parallel to or at any angle relative to the longitudinal axis L. The apertures in each test area 312, 314, 316 are preferably positioned along a straight line to facilitate insertion of a single tab 320, 322, 324 carrying the specimens into a test tube or other testing device; however, the alignment of the apertures and, thus, the shape of the tabs, may be changed to suit the particular tests or uses to be carried out on the specimens. In the present embodiment, the apertures are situated such that they are slightly off-center in their respective test area. In other words the one or more apertures are preferably positioned asymmetrically, such that a second, specimen-free portion of the tab 326 for grasping is larger than it would otherwise be if the apertures were symmetrically positioned. As with the other embodiments, this is to ensure placement of the specimen onto a portion of a removable tab while leaving a portion specimen-free for grasping in order to prevent contamination of the specimen.

The first test area 312 includes three apertures 340, 342, 344 in panel 362 for receiving specimens. Similarly, the second test area 314 includes apertures 346, 348, 350, and the third test area 316 includes apertures 352, 354, 356. The apertures are as described above, namely, the apertures are preferably circular, having a 5 mm diameter and are formed within panel 362 that is 1/16 of an inch thick.

While three apertures (e.g., 340, 342, 344) per area (e.g., 312) for receiving three specimens from each bowel movement are shown in FIG. 3, fewer or greater than three apertures can be used. For example, in one embodiment, two rows of multiple apertures per area is used.

Each of the three test areas 312, 314, 316 also has a cover 302, 304, 306 respectively, thereto along a fold line A-A extending parallel to the longitudinal axis L. Each cover 302, 304, 306 is engageable with a corresponding flap formed by arcuate slit 330, 332, 334, respectively, which is used to maintain the covers in a closed position, after the specimens are obtained. As noted, each cover may contain one or more embossed sections 380, 382, 384, that align with the one or more apertures on the first panel when the device is assembled. This is to provide additional space for collected specimens in order to prevent additional material from being removed from the device by adhering to the collected specimens.

As shown in FIG. 3, second panel 364 includes the three test areas 312, 314, 316 and further includes removable perforated tabs 320, 322, 324, respectively, each of which aligns with the corresponding apertures on panel 362. More specifically, test area 312 includes perforated tab 320 aligned with apertures 340, 342, 344; test area 314 includes tab 322 aligned with apertures 346, 348, 350; and test area 316 includes tab 324 aligned with apertures 352, 354, 356.

The portion of the tab that does not come into contact with the specimen, which is made relatively larger due to the apertures being positioned off-center (e.g., 326); is used to pull the tab (e.g., 320) away from the device. In this way, physical contact between the tester and the specimen is prevented, thereby decreasing the chance of contamination of the specimen.

The covers 300, 302, 304 for first panel 362 may be provided with appropriate printed matter to assist the patient, physician and/or laboratory. For example, the patient's name, address and instructions on how to use the device may be printed on the covers 300, 302, 304. Such instructions may include instructing the patient to apply a specimen from the same areas of the fecal matter, or even the same smear, in each of the specimen wells. Printed matter may also be provided on the second panel 364. For example, instructions to the tester as to how to remove the pull tabs 320, 322, 324 such that the fecal specimen is removed from the device.

In a further embodiment, panel 362 can be provided with indicating means for locating where specimen is to be placed on the sheet. The indicating means may comprise printed circles or other shapes on the panel as a visible indicator to the user of where to place the specimen.

With regard to the embodiment of FIG. 3, where a fecal specimen is to be acquired, the device 360 is typically sent home with a patient. The patient opens the cover 300 on the first panel 362 of the device and smears a first fecal specimen from an area of the bowel movement through one aperture 340 in test area 312, a second fecal specimen from an area of the bowel movement through second aperture 342 in test area 312, and a third fecal specimen from an area of the bowel movement through second aperture 344 in test area 312, thereby depositing specimens on the perforated tab 320, which is aligned with apertures 340, 342, 344. If desired, a second fecal specimen, for example, taken at a different time as a result of a different bowel movement or from a different region of the same bowel movement as the first specimen, is then smeared through other apertures 346, 348, 350 in test area 314 and onto the perforated tab 322. With the specimens taken, the cover 302 is closed and secured in the arcuate slit 330.

The patient obtains the requisite number of specimens and typically either returns the device to the physician or to a laboratory. Once the patient has returned the sampling device to the appropriate personnel the acquired specimens can be tested for the presence of fecal occult blood using any of the tests described herein.

Figure 4:
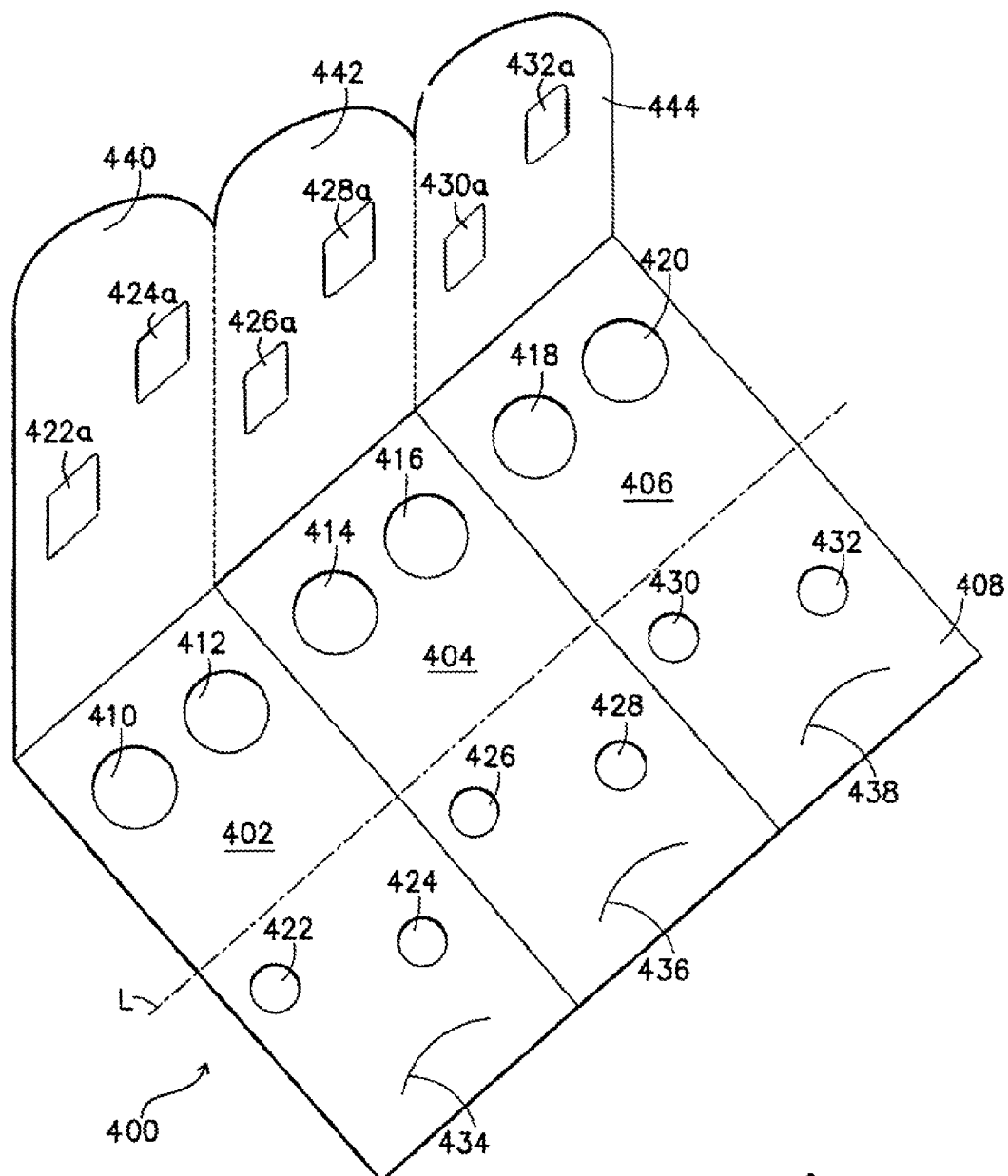
FIG. 4 is a front perspective view of a device according to another embodiment of the invention.
Figure 5:
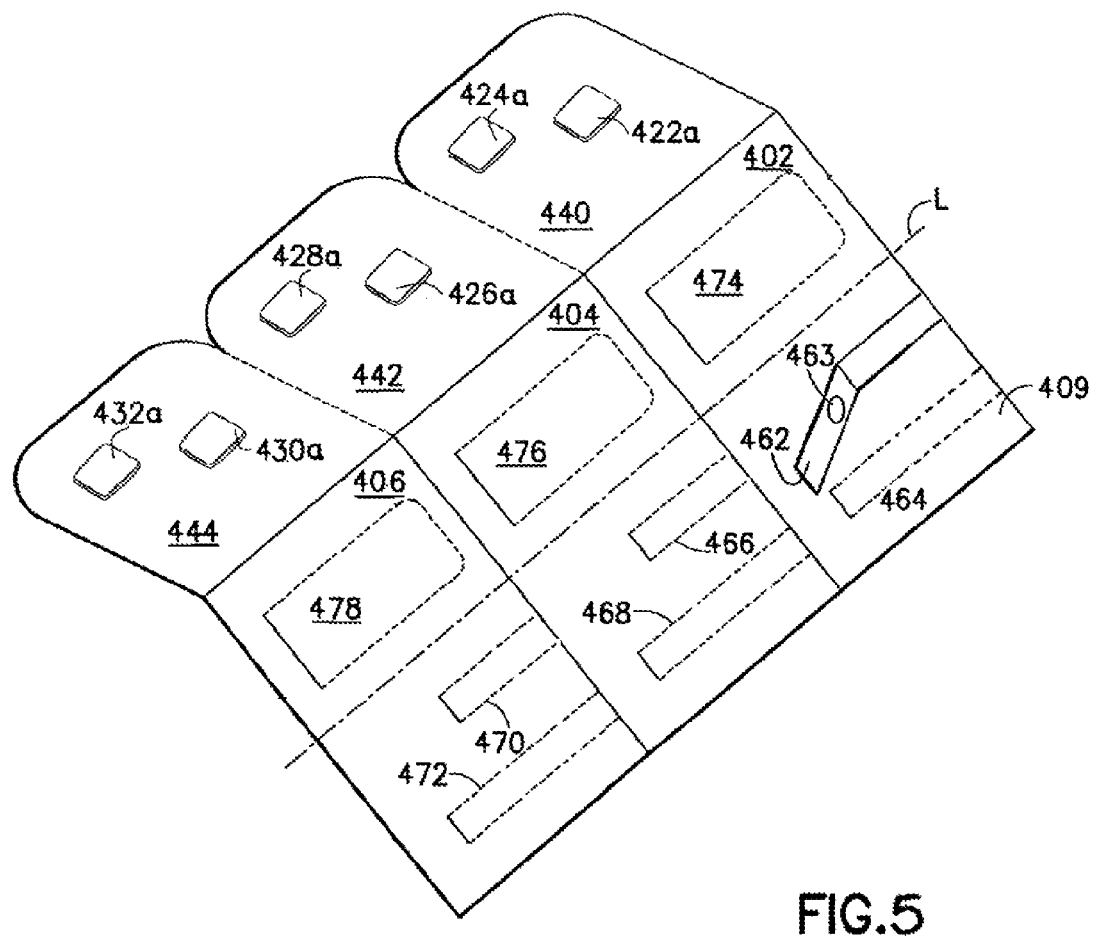
FIG. 5 is a rear perspective view of the device of FIG. 4.
Figure 6:
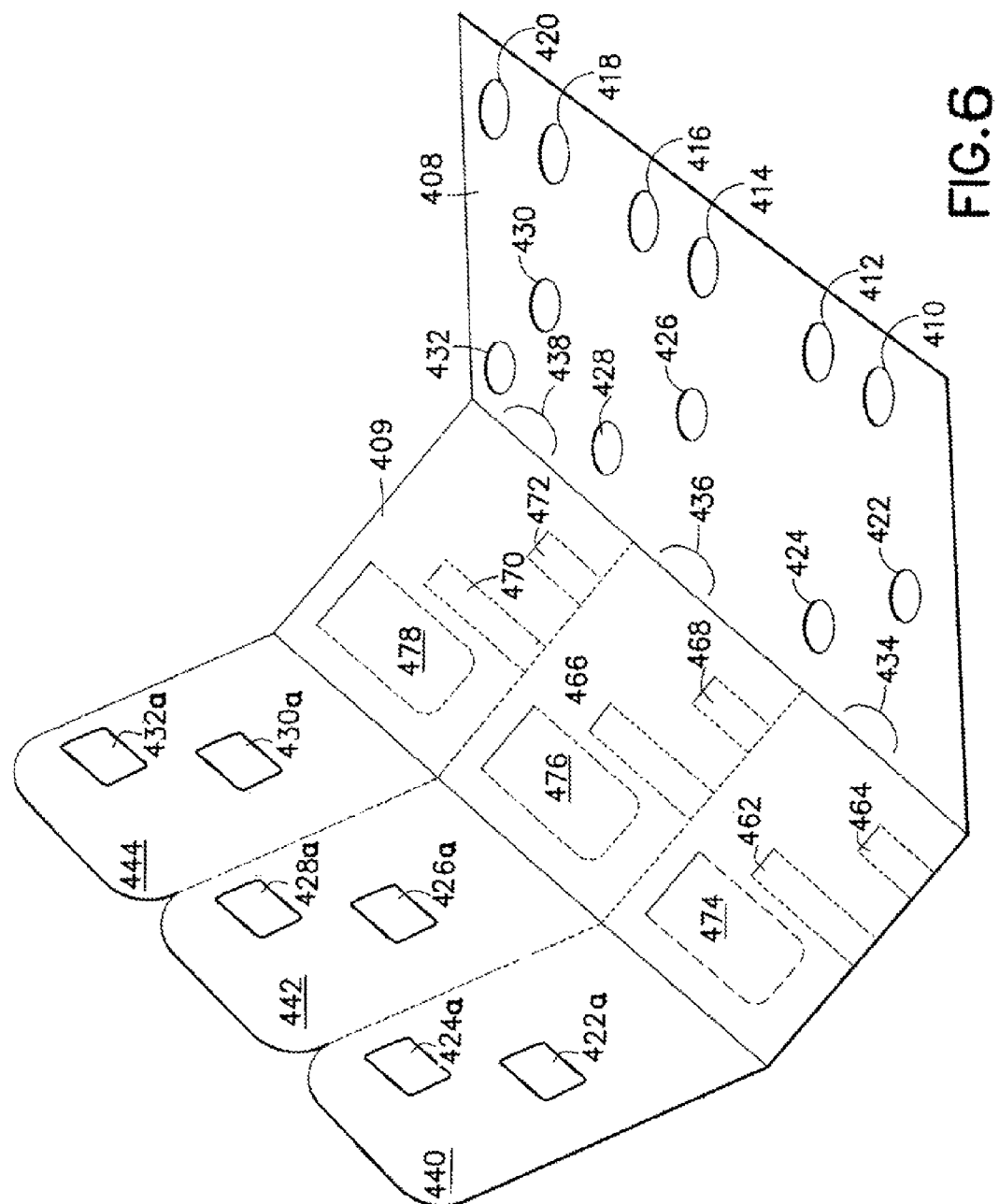
FIG. 6 is a front perspective view of the embodiment of FIG. 4 in an unassembled state.

Referring to FIGS. 4-6, a fecal occult blood testing device 400 according to one embodiment of the invention, is shown. The device 400 generally includes three test areas 402, 404, 406 (though the device may include other numbers of one or more test areas) and is formed of a first panel 408 and a second panel 409, with an absorbent sheet 8 disposed between the first and second panels 408, 409.

Each test area 402, 404, 406 is configured to receive one or more of both primary specimens and secondary specimens. The first test area 402 includes two apertures 410, 412 in panel 408 for receiving primary specimens and two apertures 422, 424 for receiving secondary specimens. Similarly, the second test area 404 includes apertures for primary specimens 414, 416 and apertures for secondary specimens 426, 428, and the third test area 406 includes primary 418, 420 and secondary 430, 432 specimen apertures.

According to the present embodiment, the apertures are round; however, as with the embodiments discussed with reference to FIGS. 1-3, in alternate embodiments the shape of the apertures on panel 408 can include, but are not limited to, an oval, square, rectangle and others, and the apertures may have the same or different shapes within a test area or among different test areas.

Each of the three areas 402, 404, 406 also has a cover 440, 442, 444, respectively, thereto along a fold line extending transversely of the longitudinal axis L. Each cover 440, 442 and 444 is engageable with a corresponding flap formed by arcuate slit 434, 436, 438, respectively, which is used to maintain the covers in a closed position, after the specimens are obtained.

Each cover also includes one or more sections 422a, 424a, 426a, 428a, 430a, 432a raised with respect to the inner surface of the cover 440, 442, 444 (for example, created by embossing the covers or removing a portion of the cover's thickness from the inner surface). The embossed sections align with the collected secondary specimens (and thus, in the present embodiment, also align with the secondary apertures 422, 424, 426, 428, 430, 432 that receive the secondary specimens) and thus function to provide more space for collected specimen when the respective covers are closed (as with the embodiment of FIG. 2). In the present embodiment, the embossed sections have a depth of 1/64 of an inch (with respect to the inner surface), although in alternate embodiments the depth may be greater depending on the tear strength of the material of the covers.

As shown in FIG. 5, each of the three test areas 402, 404, 406 further includes, on the second panel 409, perforated, removable tabs, each of which aligns with a corresponding aperture for a secondary specimen. More specifically, test area 402 includes perforated tabs 462 and 464 aligned with apertures 422 and 424, respectively; test area 404 includes tabs 466 and 468 align with apertures 426 and 428, respectively; and test area 406 includes tabs 470 and 472 aligned with apertures 430 and 432, respectively. In the present embodiment, the tabs are integrally formed from the second panel 409; however, in alternate embodiments the tabs are formed from a separate removable piece on the exterior or interior of the device (e.g., an insert between the first and second panels, an insert between the second panel and an intermediate panel between the first and second panels, a tab adhered to the external surface of the second panel, etc.).

Also shown in FIG. 5, in addition to the removable, perforated tabs 462, 464, 466, 468, 470 and 472, each of which aligns with one or more corresponding apertures for a secondary specimen, each test area 402, 404, 406 includes a flap that is aligned with the primary test area apertures of the first panel 408. More specifically, test area 402 includes a flap 474 aligned with both apertures 410 and 412 in such a way that opening of flap 474 exposes the primary test area of filter paper or sheet (not shown), which is aligned with both apertures 410 and 412. An example of such sheet is shown and described in greater detail in applicant's U.S. Pat. No. 7,833,794, hereby incorporated herein by reference. Test area 404 includes a flap 476 aligned with both apertures 414 and 416, and test area 406 includes a flap 478 aligned with both apertures 418 and 420. As discussed below, the flaps 474, 476, 478 are opened to allow a reagent to be placed on the sheet when performing the non-specific test.

As described below, each tab 462, 464, 466, 468, 470 and 472 initially is maintained in a closed position, but may be opened along the perforations (in the present embodiment, along three sides although other configurations may be used) and separated from the second panel 409. The portion of each tab that does not come into contact with the specimen (e.g., 463) is a specimen-free, grasping area, that is used to pull the tab away from the device, carrying with it the specimen. In this way, physical contact between the tester and the specimen is prevented, thereby decreasing the chance of contamination of the specimen. In alternative embodiments, the tabs are dimensioned in such a way as to allow easy deposition into a test tube/vial for use in further testing.

As illustrated in FIG. 4, the panels 408, 409 and covers 440, 442, 444, can be formed of a single sheet of paper, cardboard or other suitable material, in which the apertures, slits, tabs and perforations are die-cut. The device 400 is assembled by overlaying panel 408 on to panel 409 with the sheet therebetween. The assembly is held together with a suitable glue or adhesive. The panels 408, 409 are provided on their inner surfaces with a layer of non-stick material, typically a wax layer although other materials may be used.

Despite the inclusion of a non-stick material, it has been discovered that the covers may stick to the specimens, which, in relation to the secondary specimens, may lead to either an amount of a specimen being left on the inside surface of a cover when the corresponding tab is removed, or the removal of a piece of the inner surface of the cover when a corresponding tab is removed. To help prevent the foregoing, the present embodiment includes embossed sections 422a, 424a, 426a, 428a, 430a, 432a that align with the apertures 422, 424, 426, 428, 430 and 432 receiving the secondary specimens (forming the wells), thereby providing space for the secondary specimens when the covers 440, 442, 444, are closed. In certain embodiments, each embossed section provides a space opposite each well for receiving a secondary specimen. In this way, tabs can be removed without (or with minimal) sticking of the secondary specimens to the inner surfaces of the covers.

The covers 440, 442 and 444 for first panel 408 may be provided with appropriate printed matter to assist the patient, physician and/or laboratory. For example, the patient's name, address and instructions on how to use the device may be printed on the covers 440, 442 and 444. Such instructions may include instructing the patient to apply a specimen from the same areas of the fecal matter, or even the same smear, in each of the primary specimen wells and corresponding secondary specimen wells in a given test area. Blood is not uniformly distributed throughout the fecal matter because of the high fat content of the fecal matter. As discussed below, using the same specimen in both the primary and secondary specimen wells accounts for this and allows the secondary specimen to be used in a confirmatory testing procedure. Other printed matter that may also be provided on the first panel 408 includes for example, the specimen number and the test to be performed (e.g., primary analysis or secondary analysis). Printed matter may also be provided on the second panel 409. For example, instructions to the doctor as to how to carry out testing by opening any flaps and/or tabs on second panel may be provided.

In a further embodiment, panel 408 can be provided with indicating means for locating where specimen is to be placed on the sheet. The indicating means may comprise printed circles or other shapes on the panel as a visible indicator to the user of where to place the specimen.

In an alternate embodiment of the invention, the fecal occult blood testing device includes a single test area having at least one primary test aperture, at least one secondary test aperture and at least one corresponding perforated tab.

Those skilled in the art will appreciate, based on the present disclosure, that the devices described herein may be manufactured in any number of ways, including, for example, by (not necessarily in order) starting with a suitable paper or card stock, die cutting the apertures, flaps, tabs, slits, and perforations, embossing one or more desired areas that will align with apertures, folding the device (e.g., as described above), adding any desired sheet, and gluing the device in an assembled state.

Those skilled in the art will recognize that the methods and devices of the present invention has many applications, may be implemented in many manners and, as such, is not to be limited by the foregoing exemplary embodiments and examples. In this regard, any number of the features of the different embodiments described herein may be combined into one single embodiment, and all features of a given embodiment need not be included in other embodiments. Moreover, the scope of the present invention covers conventionally known and future developed variations and modifications to the components and materials described herein, as would be understood by those skilled in the art.

For example, in the above description, the apertures, perforated zones and tabs are illustrated as rectangular or circular. However, any desired shape may be used, for example, oval, square, rectangular or other polygon.

In the above description, the tabs are illustrated as being perforated on three sides. However, the tabs may also be perforated on fewer sides, (e.g., two sides, with a cut-out along one side) or on all sides and be punched out of the device for use in the secondary analysis of the specimens. Tabs may also be oriented in different directions.

Furthermore, although embodiments are shown with three test areas (e.g., for testing three bowel movements) with two or three specimens from each, other numbers of test areas and/or specimens may be used.

The embodiments of the invention has been described with reference to analysis of fecal specimens for stool occult blood. However, the device may be used for screening and testing of other biological specimens, for example blood and AIDS tests, urine tests and pregnancy tests.

While embodiments of the present invention have been described in considerable detail, the invention disclosed herein is not limited to the detailed description, and is to be afforded the full scope of the appended claims and all equivalents thereto.

What is claimed is:

1. A specimen collection device comprising:
    a first panel having (i) a surface and (ii) one or more apertures through the first panel for receiving specimen;
    a second panel having a removable tab, the removable tab aligned with the one or more apertures when the device is assembled such that depositing specimen through the one or more apertures deposits the specimen on the removable tab;
    a cover having one or more embossed sections defining one or more raised areas, the one or more embossed sections aligning with the one or more apertures when the cover overlays the surface of the first panel such that the one or more raised areas is provided above the surface of the first panel and aligned with the one or more apertures.

2. The device of claim 1, wherein the one or more embossed sections is a single embossed section that aligns with the apertures.

3. The device of claim 1, wherein the one or more apertures is multiple apertures and the one or more embossed sections is multiple embossed sections, each aligned with a separate one of the apertures.

4. The device of claim 1, wherein the cover has an inner surface adjacent the surface of the first panel when overlaying the first panel, and the one or more embossed sections are raised with regard to the inner surface such that the one or more raised areas exists between the surface of the first panel and the inner surface of the cover at the one or more embossed sections when the cover overlays the surface of the first panel.

5. The device of claim 1, wherein the one or more embossed sections have a thickness less than that of the cover.

6. The device of claim 1, wherein the first panel further includes one or more additional apertures and the device further comprising a sheet aligned with the one or more additional apertures for receiving a primary specimen through the one or more additional apertures for on-device testing.

* * * * *